United States Patent [19]
Kitson et al.

[11] Patent Number: 5,562,788
[45] Date of Patent: Oct. 8, 1996

[54] COMPOSITE MATERIAL LASER FLAW DETECTION

[75] Inventors: Lee E. Kitson, North Hills; Dennis K. Rock, Spring Mount; James E. Eder, Cheltenham, all of Pa.

[73] Assignee: The Boeing Company, Seattle, Wash.

[21] Appl. No.: 309,534

[22] Filed: Sep. 20, 1994

[51] Int. Cl.$^6$ ............................................. B32B 31/00
[52] U.S. Cl. ........................... 156/64; 156/378; 156/574; 250/559.07; 250/559.36
[58] Field of Search ........................... 156/64, 350, 353, 156/378, 425, 574; 250/559.07, 559.24, 559.36, 559.37

[56] References Cited

U.S. PATENT DOCUMENTS

| | | | |
|---|---|---|---|
| 4,499,383 | 2/1985 | Loose | 250/561 |
| 4,519,857 | 5/1985 | Clay | 156/64 |
| 4,699,683 | 10/1987 | McCowin | 156/353 |
| 5,110,395 | 5/1992 | Vaniglia | 156/353 |
| 5,120,976 | 6/1992 | Clayton et al. | 250/560 |
| 5,200,018 | 4/1993 | Gill et al. | 156/359 |
| 5,213,646 | 5/1993 | Zsolnay et al. | 156/166 |
| 5,239,183 | 8/1993 | Kouno et al. | 250/561 |
| 5,266,139 | 11/1993 | Yokota et al. | 156/169 |
| 5,290,389 | 3/1994 | Shupe et al. | 156/425 |

OTHER PUBLICATIONS

American Helicopter Society, Mideast Region/Technical Specialists' Meeting/Rotorcraft Composites Manufacturing/Transition Into the 21st Century, *Proceedings*, (Sep. 21–23, 1993): Kitson, L., and Rock, D., "Tow Gap Detection Using Laser Images."

SAMPE 34th Symposium, *Book of Proceedings* (May 8–11, 1989): Evans, D. O., Vaniglia, M. M., and Hopkins, P.C., "Fiber Placement Process Study" 156:574.

*Primary Examiner*—David A. Simmons
*Assistant Examiner*—Paul M. Rivard
*Attorney, Agent, or Firm*—Christensen O'Connor Johnson & Kindness PLLC

[57] ABSTRACT

A method of and apparatus for detecting flaws on a composite surface laid-up by a fiber placement machine. The invention includes a vision imaging system (78) mounted on the machine so that it has a field of view of the composite tows after they have been compacted by a compaction roller (74). In one embodiment, the visual imaging system (78) includes a laser analog displacement sensor. The imaging system provides a computer analysis system (84) with data regarding the location of the edges of the individual composite tows. The computer imaging system (84) uses the tow edge location data to compute the location and size of gaps or overlaps between the tows or the presence of foreign material. This information is useful in quality control models to evaluate the manufacturing process or final part quality.

18 Claims, 7 Drawing Sheets

COMPOSITE MATERIAL LASER FLAW DETECTION

FIELD OF THE INVENTION

The present invention relates to composite material fiber placement and, more particularly, to methods and apparatus for detecting flaws during the lay-up of fiber composite products.

BACKGROUND OF THE INVENTION

Composite materials are widely used in the fabrication of products ranging from tennis rackets to advanced aerospace structure. Composite materials are sold in various forms including sheets consisting of continuous parallel reinforcing fibers embedded in an organic matrix material. Typically, the matrix material is an adhesive, such as an epoxy resin. The sheet consisting of the reinforcing fibers and the matrix material is known as "prepreg."

Prepreg is commonly provided by a manufacturer as a continuous sheet wound on a roll or spool, with the fibers extending longitudinally around the spool. Prepreg can be purchased in widths ranging from about ⅛ inch wide to several meters wide. Typically, wider prepreg spools are used in hand lay-up procedures, in which individual layers or plies of prepreg are manually placed on top of each other by a worker. Narrower spools, commonly referred to as tapes or tows, are typically used in automated tape laying machines, fiber placement machines or winding machines. Automated tape laying machines use wider spools of prepreg on the order of inches while fiber placement machines use narrower spools on the order of ⅛ to ½ inch. Throughout this application, the terms automated tape laying machine and fiber placement machine are used interchangeably.

Fiber placement machines use a robotic arm to mechanically place individual layers or plies of composite prepreg onto an underlying substrate. Fiber placement machines are capable of starting an individual ply of prepreg at the location desired, laying up the ply over the distance desired, and then terminating or dropping off the ply at the location desired. As shown in FIG. 1, the operative end of the robotic arm terminates at a fiber placement head 10. One or more continuous spools of prepreg tape or tow are mounted on the fiber placement head. Most fiber placement machines can place a maximum of 12 to 32 tows at one time, forming a band of prepreg from 1.5 to 4.0 inches wide. The individual tows 12 are aligned and organized into a prepreg band by a band collimator 14. The collimated composite band extends through a series of rollers 16 and a tow cutter and clamp mechanism 18, as shown schematically in FIG. 1. The tow cutting and clamp mechanism 18 is capable of cutting or restarting the entire band or individual tows forming the band during the composite lay-up operation. Alter being collimated, the band of composite material passes between a compaction roller, rotatably coupled to the fiber placement head 10, and the underlying substrate 26.

As the fiber placement head 10 is moved over the substrate 26, as illustrated by arrow 28, the compaction roller 22 presses the prepreg band against the substrate. The pressure causes the prepreg band to adhere to the substrate 26. As the fiber placement head 10 moves forward, the portion of the prepreg band rearward of the compaction roller is maintained in position by the adhesive adherence between the band of prepreg and the substrate.

A fiber placement machine's use of multiple tows permits the fiber placement head to be steered along the tool surface while allowing each tow to travel at its own speed. This differential tow pay-out capability coupled with the ability to individually drop or add tows provides flexibility required by rapidly changing substrate contours and sizes.

The use of multiple tows provides increased flexibility, however it also introduces a potential for creating gaps between individual tows during placement. The fiber placement machine's ability to accurately place individual composite tows is influenced by a number of different variables including prepreg tack, the contours of the substrate, the speed at which the fiber placement head advances, the force provided by the compaction roller, the type of material, environmental conditions such as temperature and humidity, etc. These variables, along with others, often result in small gaps between the individual tows after they have been placed on the substrate.

Fiber placement machines apply the composite tows to the substrate at near-zero tension. The use of near-zero tension allows the fiber placement machines to place the tows on concave, convex, and compound surfaces. However, the use of near-zero tension also contributes to the occurrence of gaps between the edges of the individual tows after placement.

The size, location, and frequency of gaps between tows influences the quality of the resulting part. As illustrated in FIGS. 2 and 3, such gaps are generally of two different types. In some applications, as a composite band 30 is applied to the substrate, it is necessary to terminate or add an individual tow 32 in order to decrease or increase the width of the band placed. When an individual tow is terminated or added, a triangular gap 34 is formed at the terminal end of the tow 32. The size and shape of the gap 34 is partially determined by the width of the individual tows, the speed at which the compaction roller places the tows, and the ability of the fiber placement head to collimate the remaining tows.

In addition to gaps produced by adding or terminating individual tows, gaps are created during the placement process. As illustrated in FIG. 3, as a composite band 36 is placed on the substrate, the tows 38 forming the band do not always remain collimated. Sometimes, the individual tows move or slip during placement or after placement, forming gaps 40 between the edges of the tows.

The occurrence of gaps caused by dropping off or adding individual composite tows can be approximately calculated using the control data supplied to the fiber placement machine. In order to operate the fiber placement machine, it is necessary to model the surface upon which the composite prepreg is placed. Such modeling includes determining the location of all tow drop-offs and additions. Using such control data, the position and size of the triangular-shaped gap at the terminal end of terminated tows can be calculated. Software packages to perform such calculations are commercially available from such manufacturers as Cincinnati Milicron, Cincinnati, Ohio.

The occurrence of gaps due to factors other than tow additions or terminations are difficult, if not impossible, to accurately predict. Numerous physical phenomena contribute to the occurrence of such gaps. Some of the contributing variables include: (1) variations in tow widths, (2) twisted fibers or resin build-ups in individual tows, (3) the spool tension and surface adherence on each tow, (4) the steering radius of the fiber placement head or radius of curvature of the compaction. roller, (5) overlap, foreign materials, or gaps in the underlying substrate, (6) environmental factors such as temperature and humidity affecting the behavior of the individual tows, etc.

The occurrence of gaps between individual tows is also influenced by the contours of the substrate on which the tows are being placed. As illustrated in FIG. 4, gaps are less likely to occur when laying up planar surfaces, such as surface 42, and more likely to occur when laying up tows on surfaces having more complex geometries or acute radiuses of curvature. An estimate of the relative occurrence of gaps associated with surface contours is, from lowest to highest, planar surfaces 42, peak surfaces 44, ridge surfaces 46, saddle ridge surfaces 48, saddle valley surfaces 50, valley surfaces 52, pit surfaces 54, to minimal surfaces 56.

Another contributor to the occurrence of gaps between tows is the "traverse compliance" of the compaction roller. Traverse compliance is the potential for individual tows to lift from the surface of the substrate as the fiber placement head moves across the valley of a convex surface. Such lifting is commonly related to the diameter of the compaction roller compared to the bandwidth of the prepreg being placed.

When parts contain complex geometries or an acute radius of curvature, they are generally laid up manually. Alternatively, if possible they are laid up in a pattern such that the change in surface contour in the direction of movement of the fiber placement head is gradual enough to be accommodated by the fiber placement machine.

The high speed at which fiber placement machines place composite prepreg, along with the contours of completed pans, present a quality control challenge. Presently, there are no automated methods of monitoring the occurrence or size of gaps between individual tows after placement. Prior methods of quality control and assurance involve stopping the fiber placement head after each composite layer is placed and manually inspecting the resulting surface. Even with the assistance of hand-held inspection devices, prior methods are error-prone, time-consuming, costly, and questionable in terms of completeness and reliability. In addition, shutting down the fiber placement head during manual inspection reduces the efficiency of the fiber placement machine, thus adding to manufacturing costs.

Past inspection systems have been unsuccessful for a number of reasons. Black composite surfaces have light absorbent and low contrast properties which make imaging in ambient or fluorescent light extremely difficult. These characteristics eliminate consideration of many commercial vision systems as a solution for automated inspection of composites placed by fiber placement machines. This degree of difficulty is magnified by the fact that the surfaces and edges of the individual tows, unlike metallic surfaces, are not uniform. Fiber strands randomly crisscross the surface and extend out from the edges of the tows. These strands may appear as single spikes in a video profile of the composite surface. The fiber strands introduce a high level of image speckle noise that interferes with crisp edge definition using standard image analysis methods and techniques.

Another difficulty in producing accurate image data stems from sensor returns from a light source and camera mounted on a moving fiber placement head. Mounting fixed lights and cameras above the fiber placement machine or on the creel above the fiber placement head produces poor image results. The use of fixed mounts results in poor image resolution, partially-occluded surfaces, unreliable surface indexing, and introduces additional problems as the fiber placement head moves in and out of the camera's visual field of view.

Mounting the visual system on a fiber placement head having multiple degrees of freedom also introduces viewing difficulties. The varying angle of orientation between the fiber placement head and the surface of the substrate produces a varying angle of incidence between the visual imaging system and the surface of the substrate. It cannot be assumed that the line of sight of a visual imaging system will also be normal to the imaging surface, or that the surface will be flat. However, in a fiber placement machine, a visual image of some minimal quality can generally be obtained by mounting the visual imaging system on the fiber placement head. This is true because in most applications the most radical angle of incidence between the fiber placement head and the substrate is approximately 20°.

Taking image data at an instantaneous point in time requires quickly obtaining image data during operation of the fiber placement head. This is complicated by the fact that fiber placement heads can achieve high acceleration/deceleration rates. For example, a typical fiber placement head can achieve acceleration rates of approximately 40 feet/sec$^2$ in the x, y and z directions, 100 degrees/sec$^2$ changes in pitch and roll, and 50 degrees/sec$^2$ changes in yaw. In addition, if the fiber placement head is being used to place composite materials on a rotating mandrel, the mandrel may be accelerating at a rate of over 30 feet/sec$^2$. Most visual imaging systems use rapid shutter speeds or data acquisition rates that should be sufficient to overcome these speed of movement concerns. For example, many line scan cameras are capable of thousands of scans per second.

Another concern in an appropriate vision imaging system is that the registration of the image to the surface may change from one scan (frame) to the next due to the movement or vibration of the fiber placement head. This problem may be accounted for by gathering vibration data and using it in the reduction of the visual image data provided by the vision imaging system. Alternately, registration changes in the visual imaging data from frame to frame may be dampened at the pixel level.

The primary purpose of prior quality control and assurance gap detection inspections is not to improve the accuracy of the fiber placement machine. Instead, the goal of such inspections is to achieve a better measurement of the quality of the manufactured part and to quantify fiber placement repeatability within a set of statistical figures of merit.

A need exists for quality control methods and apparatus that reduce the amount of manual labor required to inspect composite materials placed by fiber placement machines. The present invention is directed to meeting this need.

SUMMARY OF THE INVENTION

The present invention is a method of and apparatus for detecting flaws in composite materials after they are placed on a substrate. The type of flaws detectable using the present invention include but are not limited to gaps between composite bands or tows, tow or band overlaps, and the presence of foreign materials. One embodiment of the invention uses an imaging system including a laser analog displacement sensor to detect flaws such as any gaps between tows. First, composite tows are placed upon a substrate by a fiber placement machine to form a surface of composite material. Raw data representative of the surface of the composite material is acquired from laser line scans taken perpendicular to the tow or band direction. A feature extraction algorithm analyzes the raw data and extracts data representative of the location of features of the individual tows, such as the tow edge locations or the presence of foreign materials. The feature data is used to determine the occurrence of gaps or overlaps between tows, etc.

In accordance with additional features of the invention, the data on tow edge locations is used to heuristically predict the position of tows at other locations. Laser line scans may be repeated at various locations over the surface of each layer of placed composite material. The resulting data may be used to generate a report providing an indication of the quality of the composite surface. The data may also be used to predict locations where gaps between adjacent tows exceed a gap tolerance.

In alternate embodiments of the invention, the laser imaging system may use a charge couple device (CCD) area-based camera, a line scan camera, or a time delay and integration (TDI) line scan camera to capture data. In CCD, TDI or line scan camera embodiments of the invention, the resulting digital image is processed and filtered in order to determine the edge locations of the individual tows and the presence of gaps between tows.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 7 is a schematic representation of a laser vision imaging system and a composite substrate;

DETAILED DESCRIPTION OF THE PREFERRED EMBODIMENT

Figure 1:
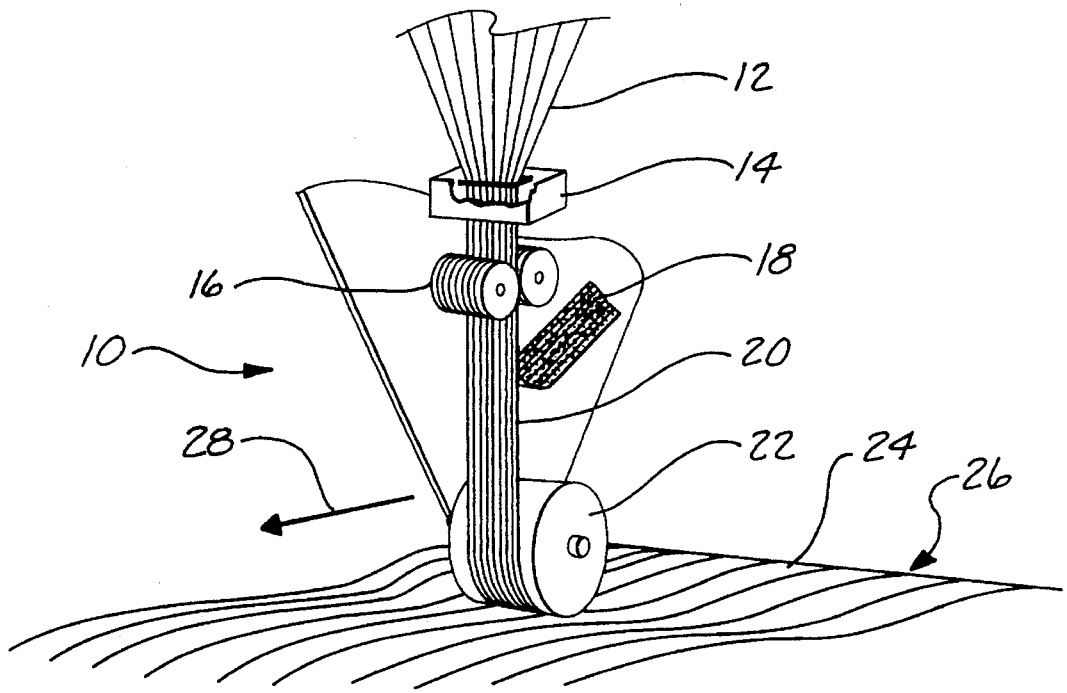
FIG. 1 is a schematic representation of a fiber placement head.
Figure 2:
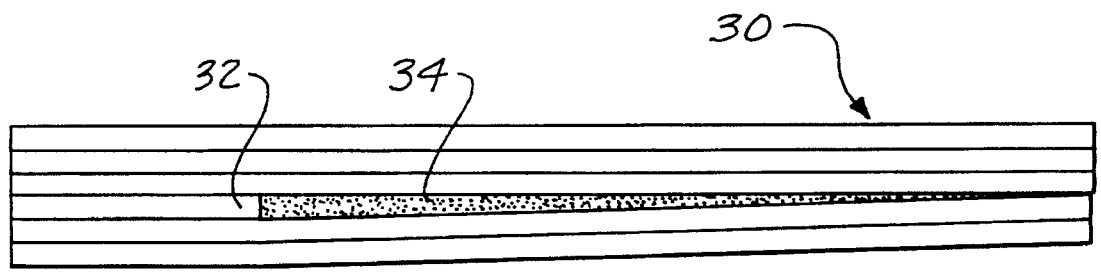
FIG. 2 is a top plan view of a band of composite material illustrating a gap between individual tows caused by a tow drop-off.
Figure 3:
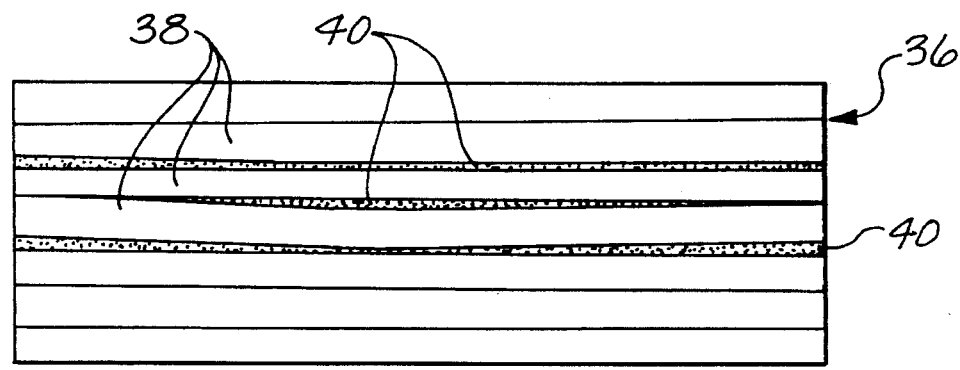
FIG. 3 is a top plan view of a band of composite material illustrating gaps between individual composite tows that are not perfectly collimated.
Figure 4:
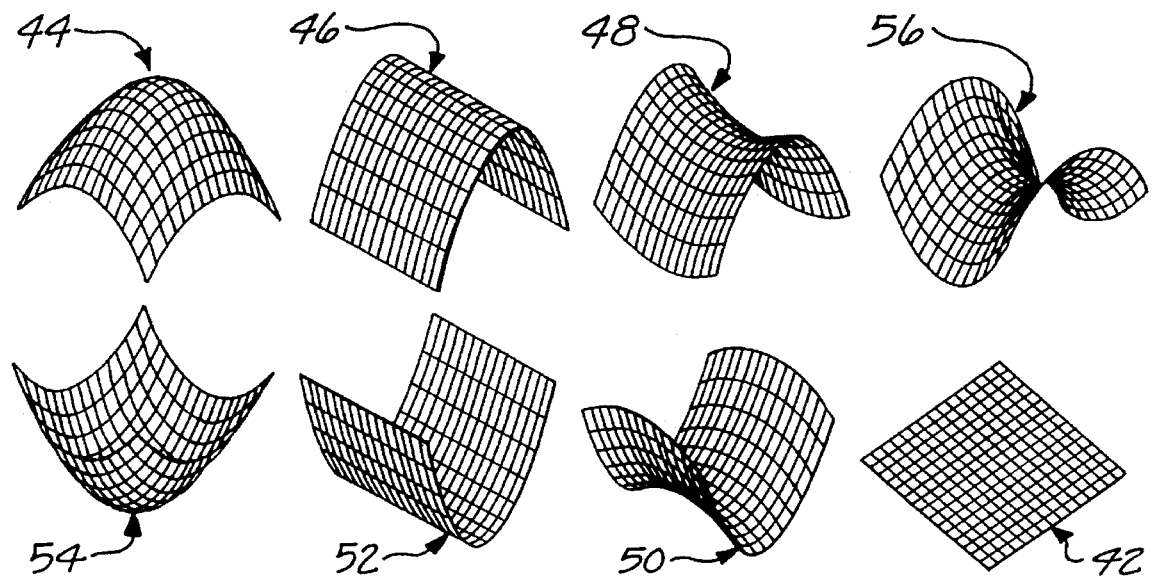
FIG. 4 is a schematic representation of various surface geometries.
Figure 5:
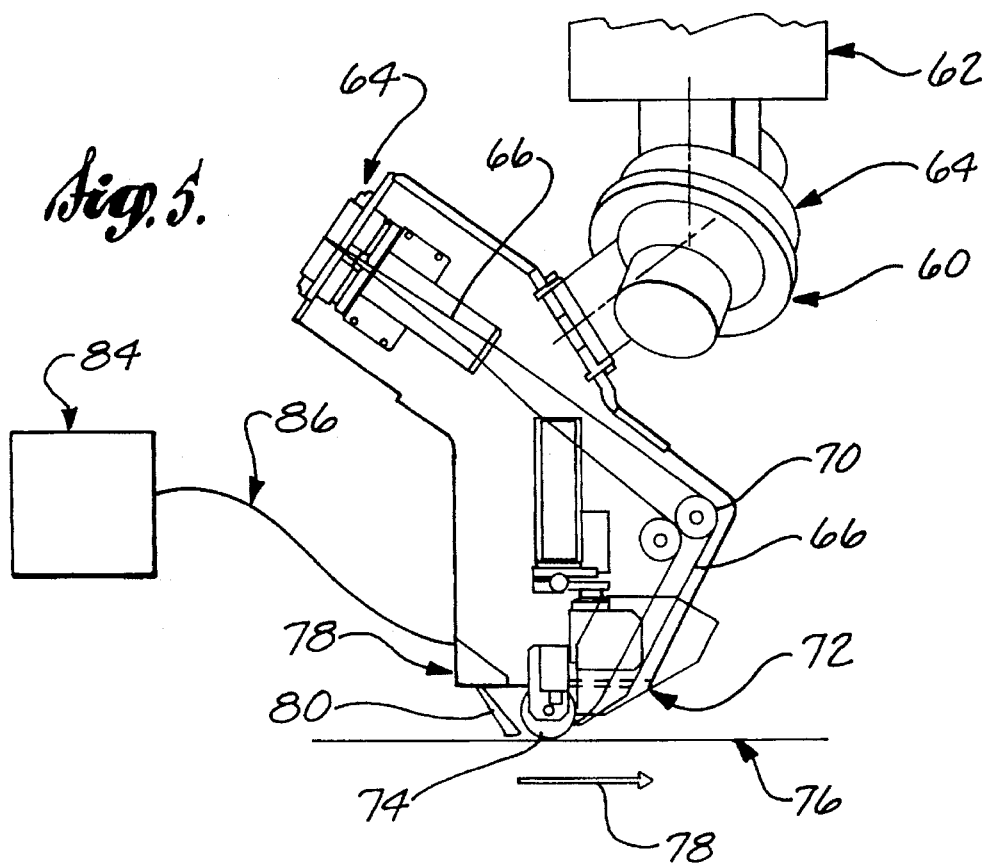
FIG. 5 is a side elevational view of a fiber placement head modified in accordance with the present invention.

A fiber placement head 60 modified according to the present invention is illustrated in FIG. 5. Since the details of fiber placement heads are well known to those skilled in the art, only a general description of the head shown in FIG. 5 is set forth here. A fiber placement head of the type shown in FIG. 5 is available from Cincinnati Milicron, Cincinnati, Ohio.

The fiber placement head 60 shown in FIG. 5 is attached to a fiber placement machine 62 (not all shown) in a manner well known in the art. The fiber placement machine 62 includes a control system and an overhead mechanical drive mechanism (not shown). The drive mechanism moves the fiber placement head up, down, forward, backward and side to side, in response to inputs from the control system. The fiber placement head 60 is attached to the overhead drive mechanism by a moveable three-axis wrist 64 that moves in response to inputs from the control system to provide an additional range of movement.

A plurality of spools of composite tows 64 are mounted on the upper end of the fiber placement head. The individual tows 66 from each spool are routed downward through the fiber placement head by a plurality of rollers 70. The individual tows 66 are collimated by a combined collimator and tow cut/clamp mechanism 72. The mechanism 72 aligns the individual tows 66 to form a uniform band of composite material. The mechanism 72 is also capable of cutting and restarting individual tows to increase or decrease the width of the band of composite material being placed on the surface of a substrate 76. The collimated band passes between a compaction roller 74 and the surface of the substrate 76 on which the composite material is being placed.

As the fiber placement head 60 moves forward over the substrate 76 as shown by arrow 78, a band of composite material is placed on and pressed against the substrate. That is, the compaction roller 74 applies a predetermined force perpendicular to the surface 76 that presses the band of composite material against the substrate, resulting in the composite material being compacted. After compaction, the band of composite material is held in place by the adhesion between the band and the substrate.

In accordance with the present invention, a vision imaging system 78 is mounted adjacent the lower surface of the fiber placement head rearward of the compaction roller 74. The location of the vision imaging system 78 is such that the field of view 80 of the vision imaging system covers the band of composite material after it is placed and compacted by the compaction roller 74. Although the preferred embodiment of the invention places the visual imaging system where indicated, alternate embodiments could place the visual imaging system at other locations. The visual imaging system 78 must be placed in a location where it will not interfere with the operation of the fiber placement head while maintaining a line of sight of the band of composite material exiting from under the compaction roller.

The vision imaging system 78 provides image data in the form of a digital signal to a computer data analysis system 84 through a suitable communication medium, such as an electrical cable 86. The computer data analysis system 84 could be an integral part of the fiber placement machine control system, or could be a separate unit. The data provided by the visual imaging system 78 is used by the data analysis system to detect the tow edges and gaps or overlaps between individual tows as described below.

Figure 6:
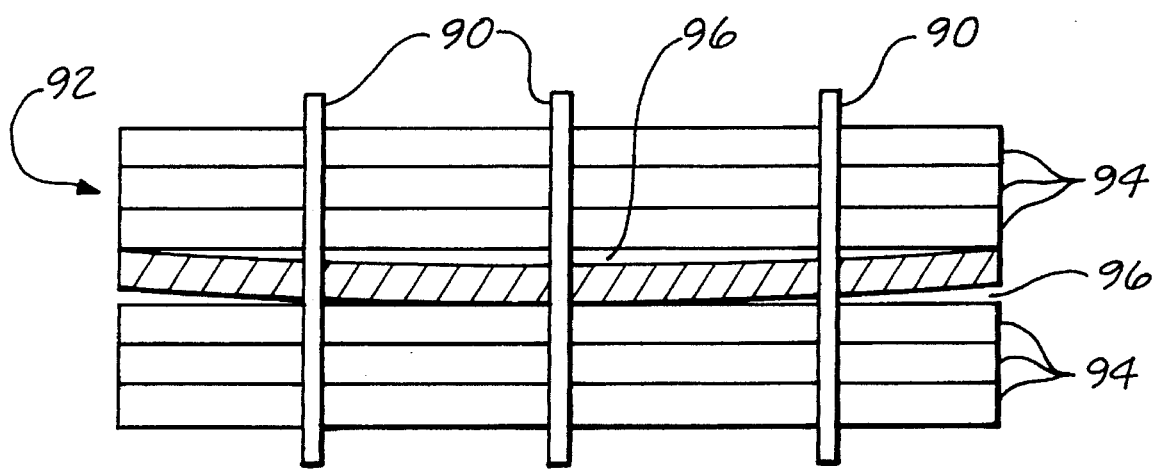
FIG. 6 is a top plan view of a band of composite material illustrating the location of laser line scans across the width of the band.
Figure 1:
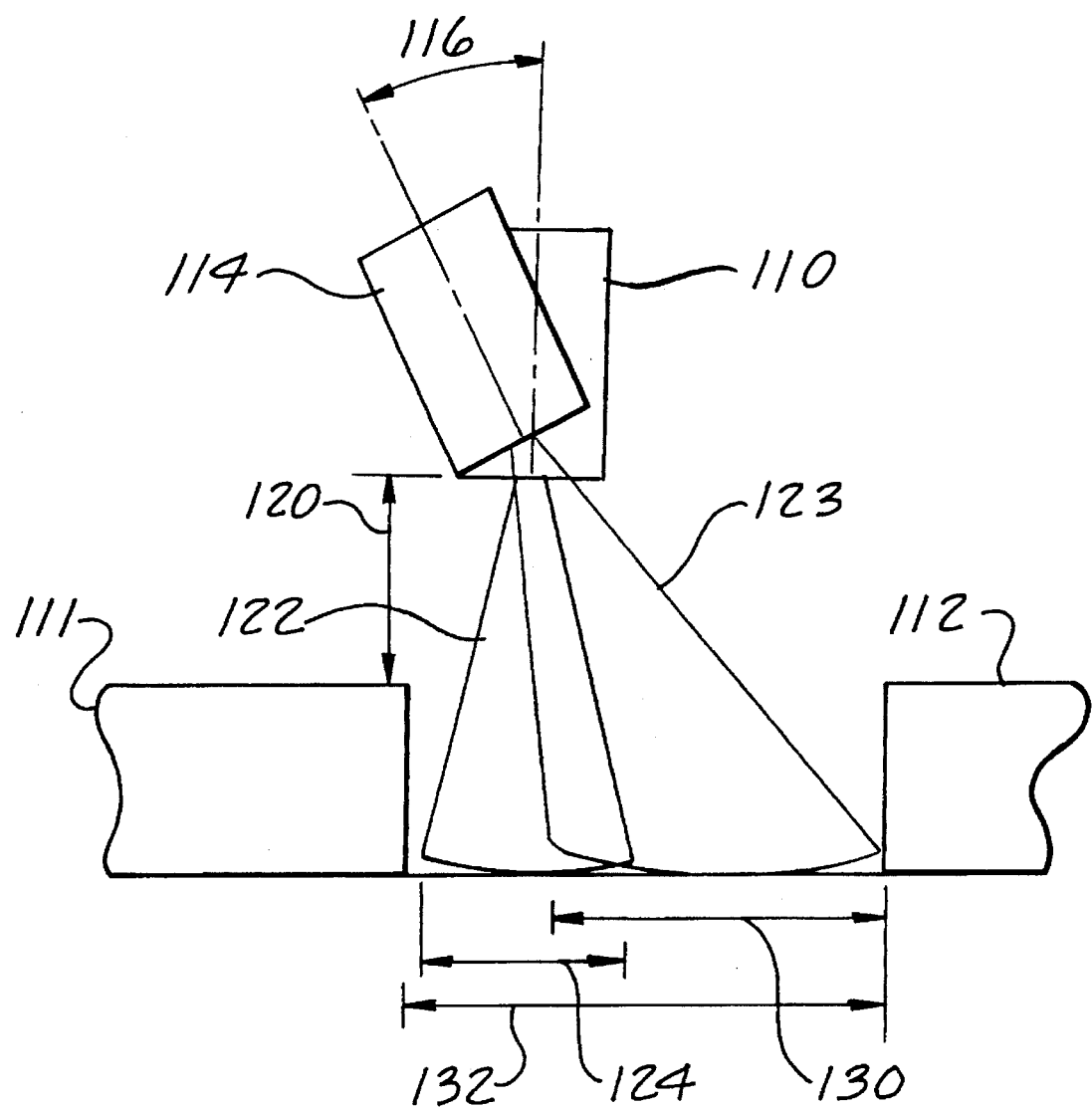

Preferably, the vision imaging system 78 includes a laser analog displacement sensor oriented to take digital image data along lines 90 across the width of a placed composite band 92, perpendicular to the tows. See FIG. 6. The digital image data is used by the computer analysis system 84 to detect the edges of individual composite tows 94 and the occurrence of any gaps 96 or overlaps between tows. Gaps and overlaps between individual tows or foreign material are interpreted from the image data as the difference in range returns using the laser analog displacement sensor. Simple triangulation methods for measuring the range distances are well known and may be used to compute the range differences.

Figure 9:
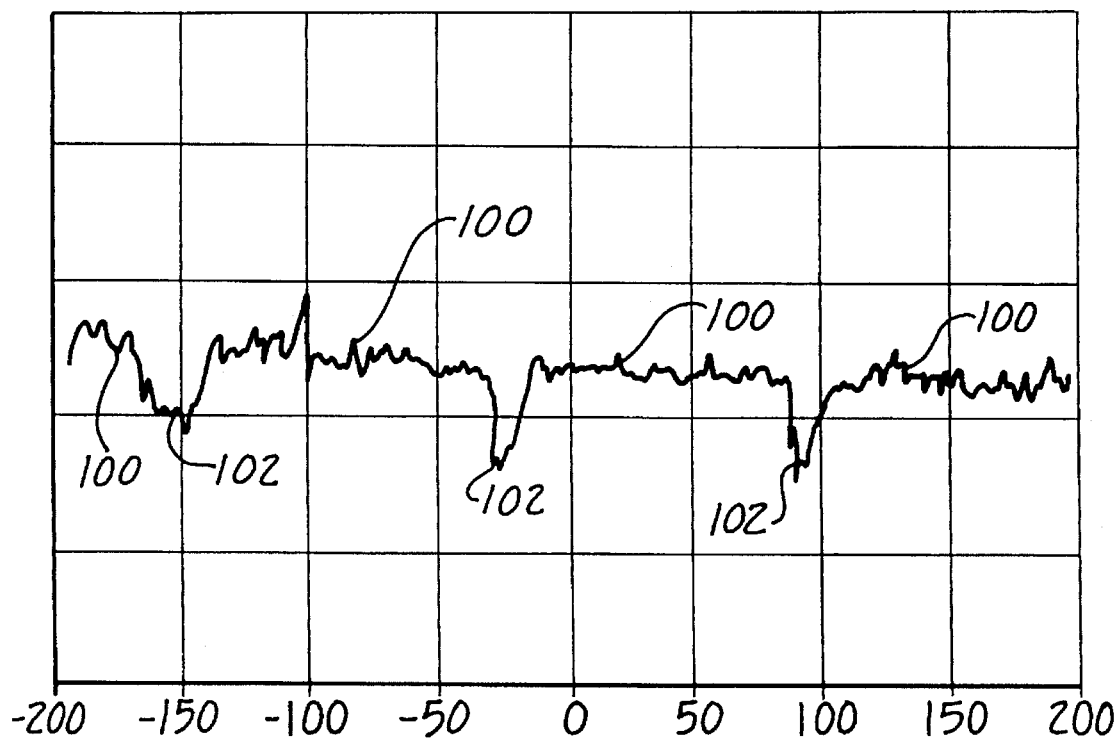
FIG. 9 is a graph of range difference versus distance across a composite band, wherein distance is represented along the x-axis and range difference is represented along the y-axis.
Figure 10:
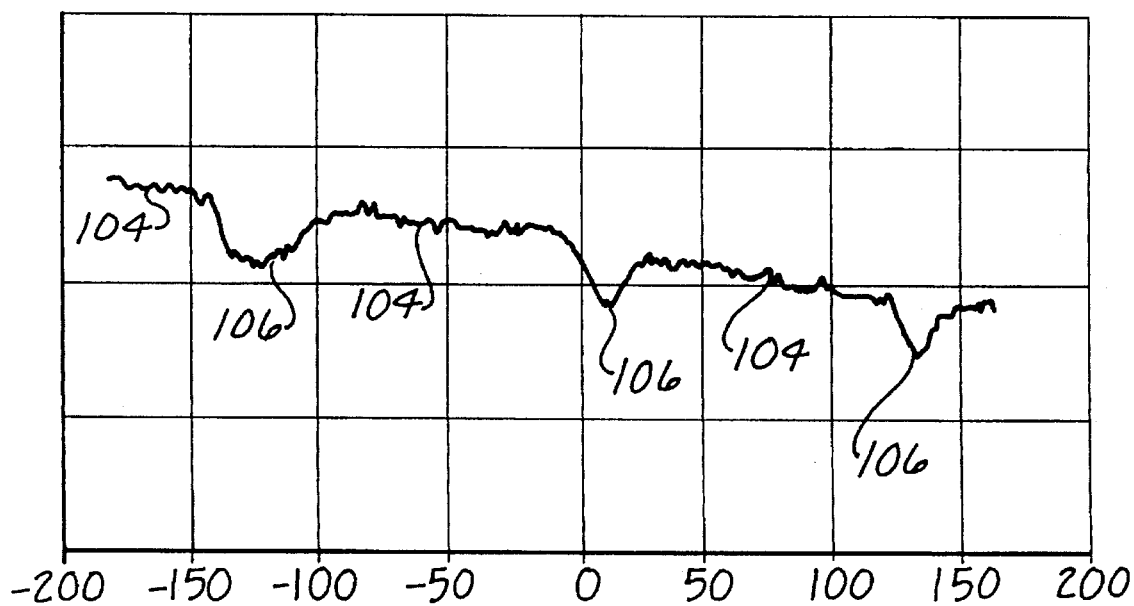
FIG. 10 is graph of range difference versus distance across a composite band, wherein distance is represented along the x-axis and range difference is represented along the y-axis.

Two representative graphs of image data produced by a laser analog displacement are reproduced in FIGS. 9 and 10. The data from the laser analog displacement sensor is represented as a graph of distance across the width of the composite band versus a nondimensionalized range return from the surface of the composite part. The distance across the width of the composite band to either side of center is represented along the x-axis in thousandths of an inch. The portions 100 of the graph (FIG. 9) forming generally horizontal lines represent the relatively uniform upper surfaces of individual composite tows. The spikes within the generally horizontal line portions 100 represent noise in the imaging system caused by lighting, composite fibers, etc. The valleys 102 in FIG. 9 represent the locations of gaps between the individual composite tows. Similarly, the generally downward sloping portions 104 of FIG. 10 represent the top surface of the tows, while the valleys 106 represent the location of gaps between individual tows.

As the imaging system 78 acquires image data, it is sent to the computer analysis system 84. The computer analysis system uses well-known data analysis techniques to determine the location of the edges of the tows and the occurrence of gaps or overlaps between the tows as described in more detail below. The fact that the laser image profiles illustrated in FIGS. 9 and 10 contain a significant amount of noise is not a primary issue of concern. Well-known image-filtering algorithms and real-time heuristic calculations of the probability of the tow locations provide methods of distinguishing between noise and actual gaps between individual tows. For example, knowledge enhanced information from one image profile can be used to "predict" the location of tows in succeeding image profiles. Likewise, efficient inspection techniques, as learned from observing the heuristics of human inspection strategies can be used to allow irrelevant data to be discarded.

In order to produce accurate image data, it is important to properly choose and position the imaging system 78. The laser analog displacement sensor's specifications, including beam divergence, "hot spot" or uneven energy distribution, and laser line thickness, should be carefully evaluated. An improper laser beam width at the surface of the composite tows being analyzed can result in questionable image resolution.

Figure 8:
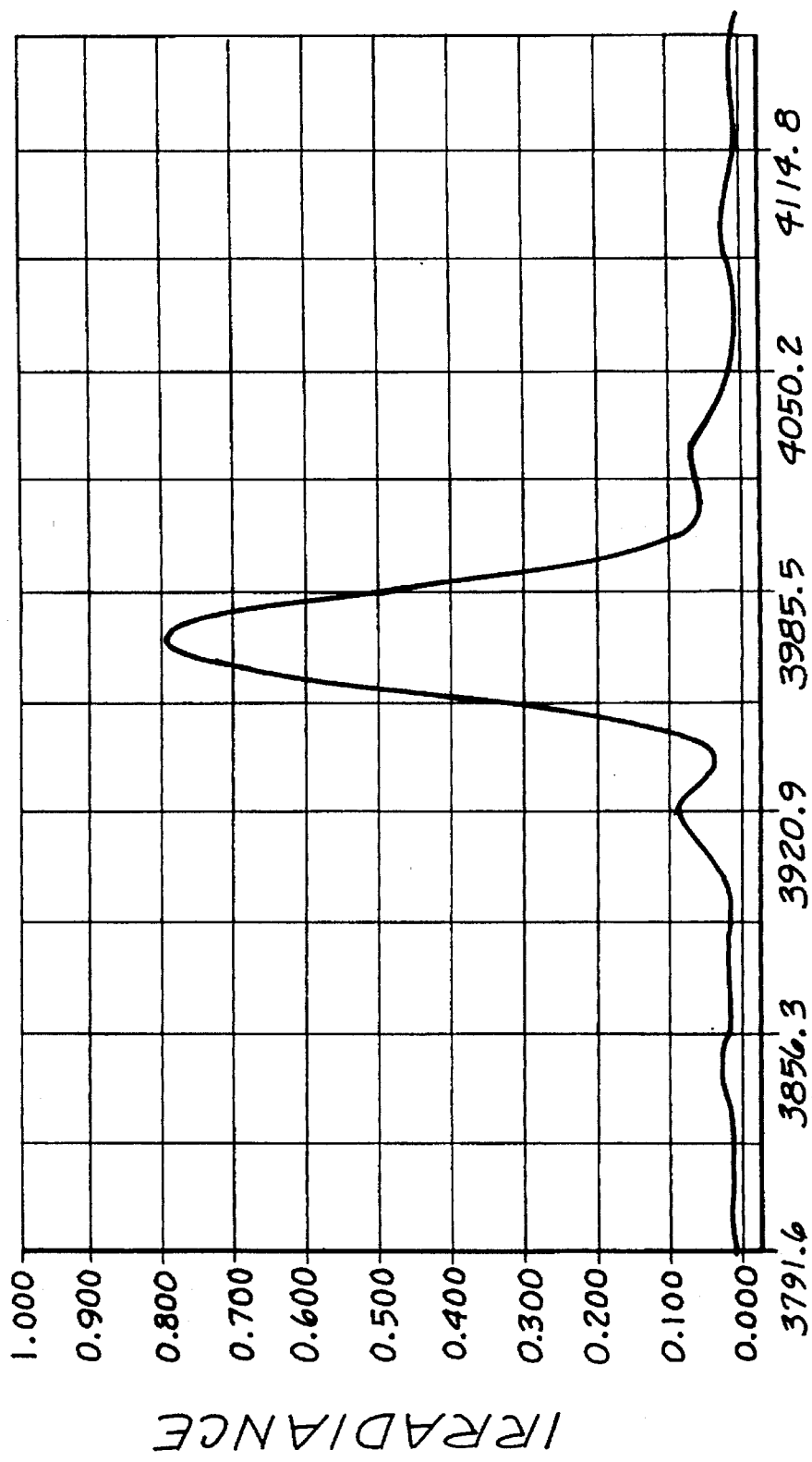
FIG. 8 is a graph of position versus irradiance for a laser data capture system, wherein position is represented along the x-axis and irradiance is represented along the y-axis.

Experimental results from a commercially available laser imaging system are illustrated in FIG. 8. The graph in FIG. 8 shows the distribution of light energy (at 5 mm aperture) in relation to beam width at a stand-off distance of 4.5 inches. A stand-off distance of 4.5 inches is approximately the stand-off distance for a vision system mounted on some commercially available fiber placement heads. As illustrated in FIG. 8, approximately 87% of the light energy from the laser analog displacement sensor falls within a line width of 55.2 microns. If the stand-off distance is reduced to 2.5 inches, the same concentration of light energy falls into a beam width of approximately 25 microns. Thus, there is a trade-off between the stand-off distance of the imaging system versus the resulting beam width on the surface being inspected. Experimental test results also show that laser analog displacement sensors produce fairly evenly distributed energy along the length of the laser line.

FIG. 7 illustrates some of the parameters that must be evaluated when choosing and positioning a laser imaging system. In FIG. 7, a first laser imaging system 110 is shown mounted perpendicular to the upper surface of two composite tows 111 and 112 (shown extending into the paper), separated by a gap 132. A second laser imaging system 114 is mounted at an angle 116 of 20 degrees off perpendicular. Both laser imaging systems are mounted at the same stand-off distance 120 from the upper surface of the composite tows. As the beam 122 from the first laser imaging system 110 defracts, it expands resulting in a beam width 124 at the lower surface of the composite tows. Similarly, the beam 123 from the second laser imaging system also defracts resulting in a beam width 130 at the lower surface of the composite tows. Due to the increased angle of incidence between the beam of the second laser imaging system and the surface of the tows, the beam width 130 is greater than the beam width 124. If the stand-off distance 120, angle of incidence 116 or resolution of the laser imaging system is improperly selected, the resulting beam width may be greater than the width of the gap 132 between the individual tows 111 and 112. In such a case, the imaging system would be unable to detect the gap 132. Thus, it is important that the laser imaging system have a narrow beam width, that the stand-off distance between the laser imaging system and the inspection surface not exceed a predetermined value, and that the divergence in beam width caused by the greatest angle of incidence expected does not result in a loss of image detail. All of the above factors must be carefully taken into account when designing the fiber placement head laser imaging system.

As illustrated in the experimental result shown in FIG. 8, the stand-off distance between the imaging system and the surface of the composite material effects system resolution. Therefore, it has been found advantageous to mount the imaging system on a compensation device that moves the imaging system toward and away from the surface of the composite material during operation. Using such a system, it is possible to maintain the stand-off distance and angle of incidence between the imaging system and the surface of the composite material approximately constant. Maintaining the distance and angle of incidence as constant as possible, reduces the possibility of errors being introduced into the image data produced.

Problems associated with motion analysis in the face of the fiber placement machine's acceleration must also be accounted for to achieve invariance to perspective. This involves estimating the relative motion of the fiber placement head with respect to the surface of the composite material being inspected, given multiple perspective projection images in the time sequence. An electronic feedback control system may be used to obtain data from the fiber placement machine regarding the machine's position, velocity, lay-up pattern, etc. An optic flow equation can then be used to define the relationship between the motion of a three-dimensional point on the surface and the corresponding motion of that point on the prospective projection image. In order to understand the prospective image projection of a point (x, y, z) on a moving rigid mandrel, the rotational and transitional velocity and acceleration must be taken into consideration. Known linear algorithms can be used to determine motion, direction of translation, and the relative position of the surface structure.

Computing optic flow or image-point correspondence between the actual structure and the visual image involves matching the prominent features of the image, e.g., fiber tow edges, from one scan to another. Several methods exist for computing these correspondences. Such methods include template match and gradient techniques. Mathematical descriptions of such methods are disclosed in Haralick, R., and L. Shapiro, *Computer and Robot Vision*, (Vol. 2), Addison-Wesley, 1993. These techniques have been used in some advanced applications requiring real time analysis of images in time-varying sequences. For example, recognizing pans on a conveyor belt uses these principles in object reconstruction by determining position, shape and geometry.

The present invention can be used to take image profiles periodically while the fiber placement machine is laying up a composite part. The image profiles may be taken at specified units of time or based on specified distances the fiber placement head has traveled. The digital data forming each image profile may be stored and analyzed by the computer analysis system 84.

The computer analysis system 84 can be used to match individual image profiles with corresponding data from the fiber placement control system regarding the position, direction, velocity and acceleration of the fiber placement head at the time each image profile was created. Thus, the present invention can be used to provide the operator or fiber placement machine with information regarding the occurrence and location of gaps throughout the composite part. Such information can be used to create a set of figures of merit on the quality of the composite surface or manufactured composite pan. Alternately, the invention can be used to create a defect map showing the locations and sizes of gaps to an operator. Ultimately, the data provided by the present invention can be used as a feedback to the fiber placement control system to increase the accuracy of the fiber placement head and thus the quality of the completed pan.

Figure 11:
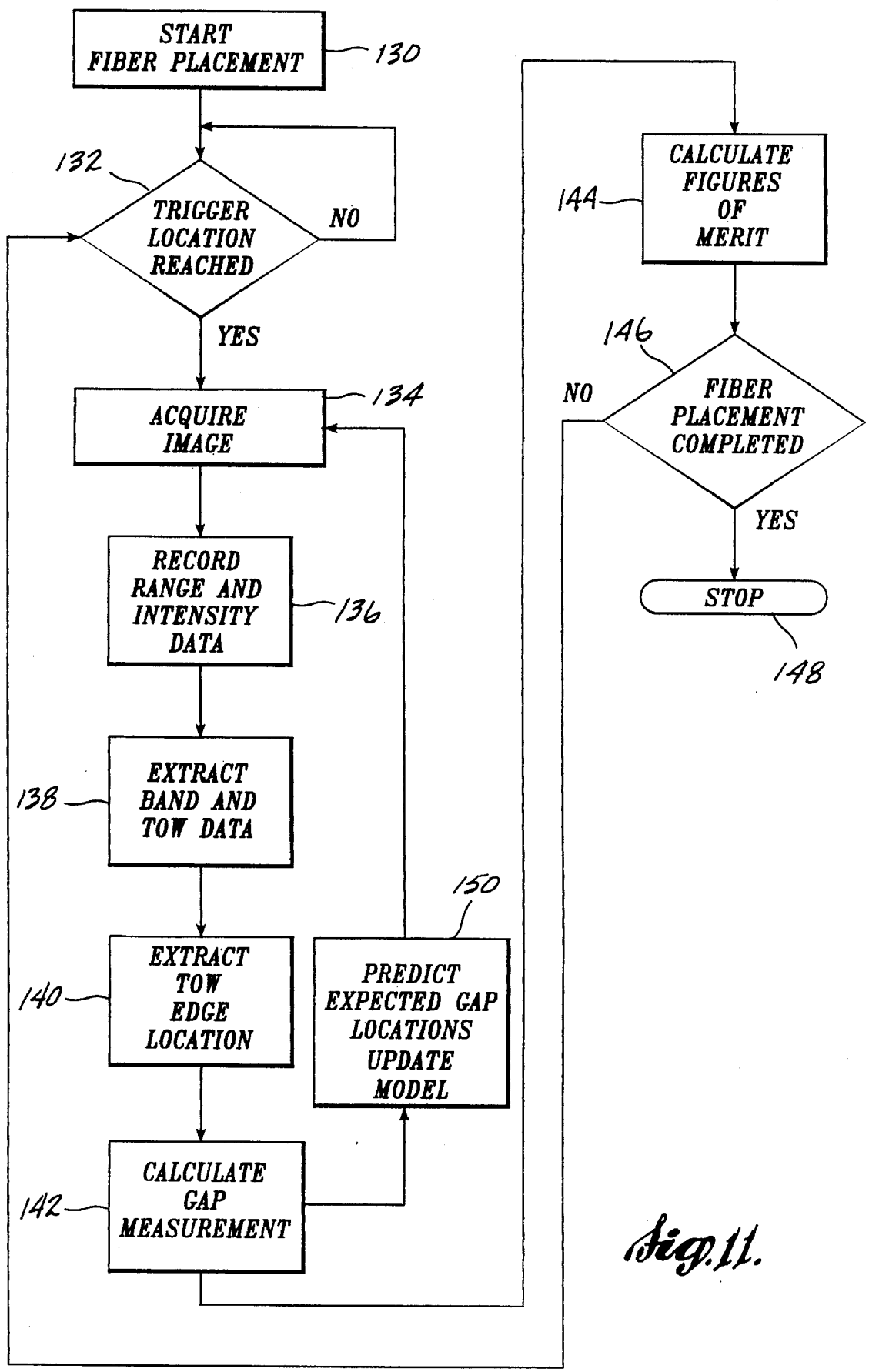
FIG. 11 is a flow chart of a method of gap detection in accordance with the present invention.

A flow chart illustrating a method of detecting flaws according to the present invention is illustrated in FIG. 11. First, in step 130, composite prepreg placement is started using the fiber placement machine. As the fiber placement head moves over the surface of the substrate, the computer analysis system inquires whether or not a trigger location where image data is to be taken has been reached, step 132. Upon reaching a trigger location, the imaging system 78 acquires an image of the placed composite material as a line scan perpendicular to the tow direction, step 134. In step 136, the digital image data including a range difference and intensity is provided to the computer analysis system.

Using image analysis tools, the computer analysis system extracts individual tow and edge location data, steps 138 and 140. Imaging analysis algorithms are available today in numerous commercial machine vision tool products. Many of these tools use modular, object-orientated programming techniques that interface to common databases. Any one of a number of these programs can be used to perform the image analysis.

The image data provided by the imaging system can be represented as feature vectors. Feature vectors are one of the simplest forms of data representation common in numerous existing machine vision applications. Feature vectors are essentially attribute-value tables, or tuples of measurements (numeric values), used for statistical pattern recognition.

At any one image profile, global attributes of the image profile can be represented by a tuple relation (band properties) with the following components: total width, location index, and quality index. These band attributes can be stored in the computer analysis system for use in various automated inspection procedures.

Once the data regarding the individual tow edge locations is calculated, it is used in step 142 to produce data representative of flaw occurrence. The resulting flaw data can then be used to calculate figures of merit, step 144, that can be used as an indication of overall part quality. The imaging system continues to process data at predetermined trigger locations throughout the operation of the fiber placement machine as shown in steps 146-148.

The computer analysis system may incorporate a software module that uses data regarding edge locations and gap measurements from individual image profiles to predict future gap or overlap locations, step 150. The information from such predictions could then be used by the system to assist in updating a model to predict future tow location and edge data. The computer analysis system could also include a software module that determines whether any measured gaps exceed a threshold value. If the threshold value is exceeded, the operator or machine controller could be alerted to take appropriate action.

One possible output of the present invention is a quality index for the placed composite surface. To calculate such an index, the computer analysis system must maintain statistics on the number of tows and the occurrence of gaps and overlaps between tows and the presence of foreign material. The boundaries of each tow can be represented in a skeleton format, without representing each individual tow pixel and noise spikes provided in the data from the visual imaging system. Individual metrics corresponding to the number of gaps exceeding a threshold width, the width of the gaps etc., can be maintained and used as a set of quality figures of merit. The data regarding gap occurrences, locations and widths can also be visually represented in an animation, rendering, geometric model, perspective views, etc. More details on such a visual representation may be seen in Kitson, L. and Rock, D., "Tow Gap Detection Using Laser Images," American Helicopter Society Mideast Region, Technical Specialists' Meeting, Rotorcraft Composites Manufacturing Transition Into the 21st Century, Sep. 21–23, 1993, the subject matter of which is incorporated by reference.

In alternate embodiments of the invention, the data capture portion of the laser analog displacement system may be supplemented or replaced by a charge coupled device (CCD) area-based camera, line scan camera, or a time delay integration (TDI) line scan camera. If a CCD, TDI, or line scan camera is used, the resulting digital image is processed and filtered in order to determine the edges locations of the individual tows in the presence of gaps between tows. Example line scan cameras that may be used in the present invention include the EG&G Reticon LC 1912, Sunnyvale, Calif. An example of an appropriate TDI camera is the Dalsa CT-EL-2048, Saint Laurent, Quebec, Canada. Most CCD area-based cameras available today do not offer fine enough resolution. One exception is Kodak's 2000×2000 CCD camera. A line scan camera essentially captures images as a one-dimensional array. Line scan cameras provide high horizontal resolution, typically 2000 to 6000 pixels. Because line scan cameras take data along only a single line, it is important to illuminate the entire line evenly. A difficulty with line scanning cameras is to properly synchronize the light source illumination with the line along which the camera takes data.

TDI line scan cameras retain the advantages of line scan cameras, while reducing problems associated with light source synchronization. TDI line scan cameras integrate linear rows of photo elements. TDI cameras also use multiple data output taps that are processed independently. In use, these single taps can be isolated for statistical evaluation of individual areas of the image, or can be used to overlap multiple cameras to produce more reliable data; for example, in areas of radical changes in surface contour.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method to detect flaws in the placement of composite tows by a fiber placement apparatus after the tows have been laid up on a substrate to form a composite surface, comprising the steps of:
   acquiring image data across at least a portion of the laid up composite surface;
   processing the image data to obtain feature data representative of the location of the edges of individual tows forming the laid up composite surface; and
   determining the occurrence of flaws in the laid up composite surface using the feature data.

2. The method of claim 1, wherein the determining step further comprises determining the occurrence of gaps between individual tows forming the laid up composite surface using the feature data.

3. The method of claim 1, wherein the determining step further comprises determining the occurrence of overlapping tows on the laid up composite surface using the feature data.

4. The method of claim 1, wherein the determining step further comprises determining the presence of foreign material on the laid up composite surface using the feature data.

5. The method of claim 1, wherein the acquiring step further comprises acquiring image tow data on the laid up composite surface using a laser analog displacement sensor.

6. The method of claim 1, wherein the acquiring step further comprises capturing image data on the laid up composite surface using a laser and a charge coupled device (CCD) camera.

7. The method of claim 1, wherein the acquiring step further comprises capturing image data on the laid up composite surface using a laser and time delay integration (TDI line scan camera.

8. The method of claim 1, wherein the acquiring step further comprises capturing image data on the laid up composite surface using a line scan camera.

9. The method of claim 1, further comprising the step of determining whether the occurrence of flaws exceed a predetermined tolerance threshold.

10. The method of claim 1, further comprising the step of producing a report indicative of the quality of the laid up composite surface using the feature data and the data representative of flaws.

11. An apparatus for detecting flaws in the placement of composite tows after they have been placed on a substrate, the apparatus comprising:
   a fiber placement machine including a fiber placement head and a control system used to place individual composite tows on the substrate;
   an imaging system coupled to the fiber placement head, the imaging system having a field of view of a portion of individual composite tows that have been placed on the substrate by the fiber placement machine to form the laid up composite surface, the imaging system producing image data representative of the laid up composite surface resulting from placement of the individual composite tows on the substrate;
   a data analysis system that receives the image data produced by the imaging system and analyses the image data to produce data representative of the occurrence of flaws on the composite surface.

12. The apparatus of claim 11, wherein the data analysis system analyzes the image data to produce data representative of the occurrence of gaps between the individual composite tows forming the laid up composite surface.

13. The apparatus of claim 11, wherein the data analysis system analyzes the: image data to produce data representative of the occurrence of overlaps between individual composite tows that have been placed on the substrate to form the composite surface.

14. The apparatus of claim 11, wherein the data analysis system analyzes the image data to produce data representative of the presence of foreign materials on the laid up composite surface.

15. The apparatus of claim 11, wherein the imaging system includes laser analog displacement sensor.

16. The apparatus of claim 11, wherein the imaging system includes a laser and a charge coupled device (CCD) camera.

17. The apparatus of claim 11, wherein the imaging system includes a laser and a time delay integration (TDI) line scan camera.

18. The apparatus of claim 11, wherein the data analysis system includes means for producing an indication of the quality of the laid up composite surface using the gap data.

* * * * *